US00PP12962P2

(12) United States Plant Patent
Michalik

(10) Patent No.: US PP12,962 P2
(45) Date of Patent: Sep. 17, 2002

(54) VARIETY OF GERANIUM PLANT NAMED 'PACDALA'

(75) Inventor: Andrea Michalik, Dresden (DE)

(73) Assignee: Elsner Pac Jungpflanzen (DE)

( * ) Notice: Subject to any disclaimer, the term of this patent is extended or adjusted under 35 U.S.C. 154(b) by 0 days.

(21) Appl. No.: 09/733,001

(22) Filed: Dec. 8, 2000

(51) Int. Cl.[7] ..... A01H 5/00
(52) U.S. Cl. ..... Plt./328
(58) Field of Search ..... Plt./325, 329, 328

(56) References Cited

PUBLICATIONS

GTITM UPOVROM Citation for 'Pacdala' as per QZ PBR 990958; Jun. 28, 1999.*

* cited by examiner

*Primary Examiner*—Kent L. Bell
(74) *Attorney, Agent, or Firm*—Webb Ziesenheim Logsdon Orkin & Hanson, P.C.

(57) ABSTRACT

A new and distinct pelargonium plant with red colored flowers above dark green foliage. The plant is suitable for pot planting.

1 Drawing Sheet

VARIETY DENOMINATION

'Pacdala'

BACKGROUND OF THE INVENTION

The present invention comprises a new and distinct cultivar of *Pelargonium×hortorum* known by the varietal name 'Pacdala'. The new variety was discovered in 1997 in a selective breeding program in Dresden, Germany. The new variety is the result of combination breeding between 25 dark leafed and middle green leafed, salmon color flowered unpatented selections from breeding group 6K-23. Plants of the new Geranium differ from plants of the breeding group in having larger flowers, darker leaves, and better branching. The new variety was first asexually reproduced by vegetative propagation in 1998 by cuttings in Dresden, Germany. The new variety has been trial and field tested and has been found to retain its distinctive characteristics and remain true to type through successive propagations.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar at an age of 6 months, grown in a pot having a 19 cm diameter. The data which defines these characteristics were collected by asexual reproductions by cuttings carried out in Dresden, Germany. The color readings were taken outdoors in shadow during summer. Color references are primarily to The R.H.S. Colour Chart of The Royal Horticultural Society of London.

PLANT

Classification:
*Botanical.*—*Pelargonium×hortorum.*
*Commercial.*—Zonal geranium.
Form: Erect.
Height from media surface to top of foliage: 35–40 cm.

Height from media surface to top of umbel: 50 cm.
Width: 30 cm.
Growth: Good branching.
Strength: Does not require artificial support.
Response time: 3.5 weeks.
Leaves:
*Size.*—8–10 cm long.
*Width.*—4.5 cm.
*Shape.*—Cordate.
*Margin.*—Entire; toothed.
*Texture.*—Smooth; some pubescence.
*Color.*—Upper surface is Green Group 137A. Lower surface is Green Group 137C. Faint zone is Greyed-Green group 189A. Rib color: Green Group 137D. Vein color: Green Group 137D.
Petioles:
*Color.*—Green Group 137C.
*Diameter.*—0.3 cm.
*Length.*—4–6 cm.
Stem/branches:
*Color.*—Green Group 138B.
*Length.*—25 cm.
*Internode length.*—3–5 cm.

THE BUD

Shape when just showing color:
*Overall.*—Spherical.
*Individual bud.*—Elliptical.
Color: Yellow-Green Group 144A.
Size when just showing color:
*Umbel.*—8–10 cm across.
*Individual bud.*—1–1.5 cm long; 0.7–1.0 cm wide.

INFLORESCENCE

Blooming habit: Semi-double.
Size of fully open bloom: 2.5–4 cm across.
Borne: Umbel; flower on pedicel; pedicel on peduncle.
Umbel:
*Diameter.*—12–15 cm.
*Depth.*—5–6 cm.
Inflorescence: 30–40 per plant per season.

Flowers:
*Form.*—Zygomorph.
*Number of petals.*—7–10.
*Petals.*—Size: Upper petals: 1.5×2 cm. Lower petals: 1.5×2 cm. Apex: Round Base: Pointed Margin: Smooth Color: Upper surface: Red Group 49A. Lower surface: Red Group 50D.
*Texture and appearance.*—Velvety.

Petaloids:
*Quantity.*—7.
*Shape.*—Small, irregularly formed.
*Apex.*—Round, but irregular.
*Base.*—Pointed.
*Margins.*—Smooth.
*Length.*—<2.0 cm.
*Width.*—0.3–0.7 cm.
*Color.*—Upper surface: Red Group 49A. Lower surface: Red Group 50D.

Sepals:
*Quantity.*—5.
*Length.*—1.0 cm.
*Width.*—3.0 cm.
*Apex.*—Pointed.
*Base.*—Wide.
*Upper surface color.*—Green Group 143B.
*Lower surface color.*—Grey-Brown Group 199B.

Pedicel:
*Length.*—2.5–3 cm.
*Color.*—Grey-Brown Group 199A.

Peduncle:
*Length.*—12–14 cm.
*Color.*—Varies between Yellow-Green Group 148A–148B.

Disease/pest resistance: No susceptibility to diseases or pests has been noted to date.

Lasting quality: Long-lasting; 4 weeks per umbel.

REPRODUCTIVE ORGANS

Stamens:
*Anthers.*—3 mm long.
*Filaments.*—Length: 0.5 cm maximum. Color: Pink. Pollen: Orange-red.

Pistils:
*Number.*—One with five parts.
*Length.*—0.3–0.4 cm.
*Stigma.*—Pink.
*Style.*—0.8 cm long.

Ovaries:
*Color.*—Greenish.
*Length.*—0.4 cm.

Fruit: Very rarely present. When preset, consists of 5 single seeds, break-shaped, 4 cm long, brown.

GENERAL CHARACTERISTICS

1. Dark-leafed.
2. Very insensitive against transport.
3. Good rooting.
4. Compact growth.
5. Stark contrast between leaf and flower color.
6. Very suitable for pots.
7. Flowering season is spring until frost.

I claim:

1. A new and distinct variety of geranium plant substantially as shown and described.

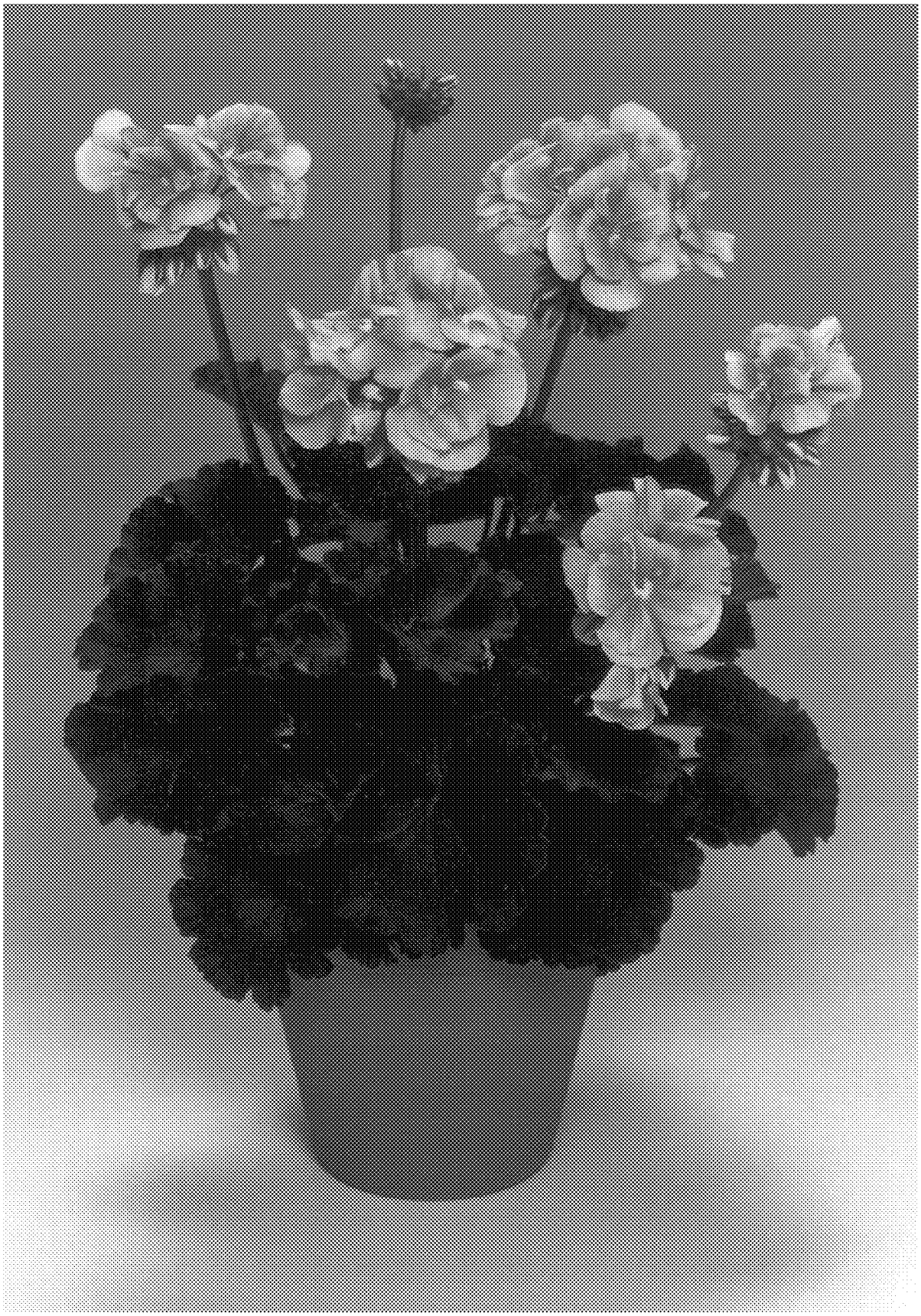

* * * * *